United States Patent [19]

Aicher et al.

[11] 4,010,208

[45] Mar. 1, 1977

[54] PRODUCTION OF FORMALDEHYDE

[75] Inventors: Albrecht Aicher, Frankenthal; Hans Haas, Ludwigshafen; Heinrich Sperber, Ludwigshafen; Hans Diem, Ludwigshafen; Guenther Matthias, Ludwigshafen; Gunter Lehmann, Ludwigshafen, all of Germany

[73] Assignee: BASF Aktiengesellschaft, Ludwigshafen (Rhine), Germany

[22] Filed: Apr. 25, 1974

[21] Appl. No.: 464,182

[30] Foreign Application Priority Data

May 5, 1973 Germany .......................... 2322757

[52] U.S. Cl. .......................... 260/603 HF; 260/606
[51] Int. Cl.$^2$ .......................................... C07C 45/02
[58] Field of Search ............................ 260/603 HF

[56] References Cited

FOREIGN PATENTS OR APPLICATIONS 1,231,229 12/1966 Germany ...................... 260/603 HF
1,294,360 3/1969 Germany ...................... 260/603 HF

*Primary Examiner*—James O. Thomas, Jr.
*Assistant Examiner*—G. T. Breitenstein
*Attorney, Agent, or Firm*—Johnston, Keil, Thompson & Shurtleff

[57] ABSTRACT

The production of formaldehyde by oxidizing dehydrogenation of methanol in the presence of a silver catalyst which consists of three or more layers each of specific weight and particles of specific particle size and having a specific total layer thickness. Formaldehyde prepared according to the process of the invention is a disinfectant, tanning agent, reducing agent and valuable starting material for the production of synthetic resins, adhesives and plastics.

10 Claims, No Drawings

PRODUCTION OF FORMALDEHYDE

The invention relates to a process for the production of formaldehyde by oxidative dehydrogenation of methanol in the presence of a silver catalyst which consists of three or more than three layers each having a specific weight and particles of a specific particle size and which has a specific total layer thickness.

Various methods for the production of formaldehyde by oxidative dehydrogenation of methanol in the presence of a silver catalyst at elevated temperature are described in Ullmanns Encyklopadie der technischen Chemie, volume 7, pages 659 et seq. An arrangement of the catalyst in a layer having a thickness of from 10 to 15 mm is described in Fiat Report No. 999, pages 1 to 3. Granules having a particle size of from 1.25 mm to 0.15 mm are used in a single layer, the coarser granules being at the bottom. The normal life of the catalyst is six months. If methanol of high permanganate reactivity is used the life may, however, fall to two months or less. Conversion of the methanol is about 94% and the yield of formaldehyde is 82.5% of theory.

BIOS Report No. 978, pages 2 to 6, discloses a four-layer catalyst of the following composition, the coarser particles being situated at the bottom of the layer:

| Particle size in mm | % by weight of total catalyst |
|---|---|
| 0.15 | 8 |
| 0.32 | 44 |
| 0.64 | 36 |
| 1.23 | 12 |

The total layer thickness is about 10 mm. The life of the catalyst depends on the quality of the methanol. A purified methanol is used; crude methanol is treated with permanganate and then distilled. The Report discloses that the catalyst usually has a life of six months. In agreement with this the abovementioned FIAT Report teaches that the life may fall to 2 months or less when methanol of high permanganate reactivity (i.e. crude methanol) is used. A yield of 82.2% of the theory is generally obtained.

German Pat. No. 1,231,229 discloses a two-layer catalyst of which the lower layer consists of at least 50% by weight of crystals of the particle size from 1.25 to 5 mm. Crystals of from 0.2 to 1 mm are used for the upper layer. The thickness of the lower layer is from 15 to 50 mm. The thickness of the upper layer given in Example 2 is from 1 to 2 mm. The life of the two-layer catalyst is given in Example 2 as 91 days and the yield as 88.3% of theory.

In the procedure described in German Printed Application (DAS) No. 1,294,360 a two-layer catalyst is used whose lower layer consists of at least 50% by weight of crystals of particle sizes from 1 to 4 mm and whose upper layer consists of crystals of particle sizes of from 0.1 to 0.9 mm. The lower layer has a thickness of from 15 to 40 mm and the upper layer has a thickness of from 0.75 to 3 mm. As the Examples show there is used as the lower layer 94% by weight of the total catalyst with particle sizes of from 1 to 3 mm, and a catalyst life of 70 days and a yield of 89% are achieved.

In the production of formaldehyde, especially on an industrial scale, an individual result of the process, for example the yield of end product, is not important in itself. It was therefore an object of the present invention to provide a process which offers as good a yield as possible, better space-time yields of end product, long catalyst life and which at the same time gives the lowest possible amount of methanol and of formic acid formed in the reaction, even when crude methanol is used. Although the methods mentioned above have certain advantages, for example the high yield in the case of the method described in DAS No. 1,294,360, they are unsatisfactory as far as the overall result is concerned. The overall result is in turn determined, in an unpredictable manner, by a number of factors some of which are interdependent, for example particle size, layer thickness, particle size distribution, pressure, temperature, volume-space velocity of the catalyst. It is impossible to deduce optimum values for the individual factors from the prior art.

German Pat. No. 1,285,995 discloses a method in which a silver catalyst is used which is composed to the extent of seven-eighths of its weight of silver crystals having a diameter of from 0.75 to 3 mm and to the extent of one-eighth of silver crystals having a diameter of less than 0.3 mm, an the reaction gas is cooled very rapidly so that the carbon monoxide content of the offgas does not rise above 0.23% by volume.

The object of this invention is to provide a new process for achieving in a simple and economical manner a better overall result in relation to yield, space-time yield, end product purity and catalyst life, especially when crude methanol is used.

We have now found that formaldehyde is obtained advantageously by oxidative dehydrogenation of methanol in the presence of a silver catalyst at elevated temperature by carrying out the reaction with a catalyst having a total layer thickness of from 15 to 35 mm and comprising three or more than three layers of silver crystals in which one portion of the layers contains from 72.5% to 89% by weight of the catalyst having a particle size of from 1 to 2.5 mm, another portion of the layers contains from 2.5 to 7.5% by weight of the catalyst having a particle size of from 0.75 to 1 mm and the remaining portion of the layers contains from 8.5 to 20% by weight of the catalyst having a particle size of from 0.2 to 0.75 mm.

In comparison with the four art methods described above the process of the invention surprisingly gives, in a simple and economical manner, a better overall result as regards yield, space-time yield, end product purity and catalyst life, especially when crude methanol is used. The life of the catalyst is as a rule at least 100 days when crude methanol is employed. All these advantageous results are surprising in view of the prior art, particularly the teaching of the BIOS Report, because it would have been expected that a considerably larger proportion of particles having particle sizes of less than 0.64 mm and a thinner layer would be necessary.

In comparison to the method described in German Pat. No. 1,285,995 the catalyst according to the invention has a longer life and can be obtained in a simpler and more economical manner. Silver crystals of all particle sizes, such as are also obtained in the electrolytic production of silver granules, may be used. Particle sizes of from 0.3 to 0.75 mm are not used in the above-mentioned method. In electrolytic manufacture or regeneration, considerable amounts of particles of the said sizes are obtained, for example up to 50% by weight of the total granules, and have to be returned to the electrolysis after every manufacturing operation.

The electrolysis unit is therefore better utilized in the process according to the invention and may be therefore made smaller; utilities, personnel and auxiliary materials, for example nitric acid, are cut and operations such as washing, screening and drying the silver are simplified. Moreover the catalyst according to the present invention has only to be heated to 280° to 300° C by an external heat source (cf. column 3, lines 40 to 42 of the Patent Specification) in order to initiate the reaction and this saves plant, energy and operating costs. Additional instrumentation for controlling the carbon monoxide content of the offgas is unnecessary.

Suitable starting materials for the process include pure methanol, technical-grade methanol, crude methanol prepared by a high or low pressure method or advantageously mixtures of the same with water; the concentration of the aqueous mixtures may conveniently be from 60 to 95% by weight and preferably from 70 to 90% by weight. In an advantageous embodiment use is made of crude methanol which has been purified according to the methods disclosed in German Printed Application (DAS) No. 1,277,834, German Pat. No. 1,235,881 and German Pat. No. 1,136,318 by separation of a low boiling fraction and/or by treatment with oxidizing agents and/or alkalies.

The crude methanol is supplied to the reaction chamber in vapor form advantageously mixed with steam and if desired with inert gas. Nitrogen is an example of an inert gas suitable for the process.

Oxidizing agents include pure oxygen or a gas containing free oxygen, particularly air. Oxygen, usually in the form of air, and methanol are conveniently used in a molar ratio of from 0.25 to 0.6 mole and particularly from 0.35 to 0.5 mole of oxygen per mole of methanol. The total amount of steam is preferably not more than 3.0 and advantageously from 0.67 to 1.75 moles per mole of methanol.

The overall layer thickness of the catalyst is from 15 to 35 mm and preferably from 20 to 30 mm. The catalyst particles in the form of crystals of silver are arranged, depending on particle size, in an upper, central or lower portion of the total layer in a reactor which is usually positioned vertically. The initial mixture of methanol vapor and oxygen, or air with or without steam and inert gas, is generally passed downwards so that the upper portion (upper layers) is the one facing the starting mixture. In reactors of other design or operated in other ways all statements in the description concerning the upper (lower) portion of the catalyst apply, mutatis mutandis, to the portion facing the incoming starting mixture (the effluent reaction mixture), for example in the case of a horizontal reactor the front (rear) portion of the catalyst. From 72.5 to 89% and preferably from 77.5 to 82.5% by weight of all catalyst particles are located in the lower portion, from 2.5 to 7.5% and preferably from 4.5 to 6.5% of all catalyst particles are situated in the central portion, and from 8.5 to 20% and preferably from 13 to 16% by weight of all catalyst particles are in the upper portion. The particles in the lower portion of the layer have a particle size of from 1 to 2.5 mm, in the central portion of the layer from 0.75 to 1 mm and in the upper portion of the layer from 0.2 to 0.75 mm. Each portion of the layer may consist of one layer or more than one layer, preferably of one, two or three layers. A catalyst consisting of from four to seven layers, and particularly of four or five layers, is preferred. Each layer differs from the other layers in the particle size of the silver crystals and usually also in the proportion of its weight to that of the whole catalyst.

If the upper portion has two layers, the lower layer preferably has a proportion of from 0.5 to 2% by weight and particles of a particle size of from 0.2 to 0.4 mm, and the upper layer has a proportion of from 8 to 18% by weight of particles of a particle size of from 0.4 to 0.75 mm. When the upper portion is composed of three layers the following are preferred in relation to the proportion by weight of the total catalyst (and particle size of the particles): lower layer 0.5 to 2% by weight (0.2 to 0.4 mm); central layer 5 to 10% by weight (0.4 to 0.6 mm); upper layer 3 to 8% by weight (0.6 to 0.75 mm). Correspondingly, in the case of the central portion the following are preferred with regard to the proportion by weight (and particle size) of the particles:
(a) Two layers:
  upper layer from 1.5 to 4.5% by weight (0.75 to 0.9 mm);
  lower layer from 1 to 3% by weight (0.9 to 1 mm).
(b) Three layers:
  upper layer from 0.5 to 1.5% by weight (0.75 to 0.8 mm);
  central layer from 1 to 3% by weight (0.8 to 0.9 mm);
  lower layer from 1 to 3% by weight (0.9 to 1 mm).
The following are preferred for the lower portion:
(c) Two layers:
  upper layer: from 7.5 to 22.5% by weight (1 to 1.75 mm);
  lower layer: from 50 to 81.5% by weight (1 to 2.5 mm).
(d) Three layers:
  upper layer: from 5 to 16.5% by weight (1 to 1.5 mm);
  central layer: from 28 to 42% by weight (1.5 to 2.0 mm);
  lower layer: from 28 to 42% by weight (2.0 to 2.5 mm).

Stratification of the individual layers is usually uniform so that the thickness of each individual layer is equal over the entire cross-section of the layer. In this case the thickness of the layer is directly dependent on the abovementioned proportion of the weight of the whole catalyst and the particle size of the particles. All or some of the layers or conveniently of one layer may be irregularly stratified, for example most of the catalyst particles may be supplied to the middle, the sides or, advantageously, the periphery of the layer and only the smaller remaining amount is distributed over the remainder of the layer. In a preferred embodiment a plurality of layers or advantageously one individual layer is arranged only at the periphery of the catalyst zone in the form of an annular layer having a level upper and lower side on the underlying, uniform layer. The following arrangement is advantageous: The upper layer (Layer 1) of the catalyst has placed on it, at the edge, an annular layer; the breadth of the annular layer (i.e. the difference between the radius of the outer circle and the radius entire of the inner circle of the annular layer) is from one hundredth to one tenth the radius of the catalyst layer and thus of the upper uniform layer. A particularly preferred arrangement is to position such an annular layer not on the upper layer (Layer 1) but beneath it, i.e. on the layer below the upper layer (Layer 2). In this way the annular layer and layer 1 (or layer 1, annular layer and layer 2) assume the shape of a flat dish having a raised edge. If the upper portion contains more than one layer, for example two or three layers, the annular layer may be placed beneath any layer of the upper portion, for example beneath layer 2 to 3. Since the reactors used are usually tubular reactors or tube-shaped reaction chambers, the said edge will be at the periphery of the catalyst support and against the inner wall of the tube.

A particularly advantageous catalyst has the following composition (layer 2 is an annular layer having a radius which in one sixtieth of the radius of the catalyst layer and which is beneath layer 1 and therefore on layer 3):

Layer 1: (uppermost)
8 to 18% by weight of the catalyst having particles of a particle size of from 0.4 to 0.75 mm;

Layer 2:
0.5 to 2% by weight of the catalyst having particles of a particle size of from 0.2 to 0.4 mm;

Layer 3:
2.5 to 7.5% by weight of the catalyst having particles of a particle size of from 0.75 to 1.0 mm;

Layer 4:
7.5 to 22.5% by weight of the catalyst having particles of a particle size of from 1.0 to 1.75 mm; and Layer 5: (lowermost)
50 to 81.5% by weight of the catalyst having particles of a particle size of from 1.0 to 2.5 mm.

Conveniently, from 1 to 3 metric tons and particularly 1.4 to 2.4 metric tons of methanol per m² of catalyst bed is passed over the catalyst per hour. In industry, it is preferred to use a catalyst bed diameter of at least 0.5 meter and conveniently from 1 meter to 3 meters.

In other respects oxidation is carried out in conventional manner; for example a gas mixture of methanol vapor, air, if desired inert gas and conveniently steam in the abovementioned amounts is passed at a temperature of from about 550° to 750° C and particularly at from 600° to 710° C through the silver catalyst. The process is generally carried out continuously at a pressure of from 0.5 to 2 atmospheres and preferably at from 0.8 to 1.8 atmospheres. It is advantageous to cool the reaction gas leaving the catalyst zone within a short time, for example down to a temperature of 350° C. The cooled gas mixture is then conveniently passed to an absorption tower in which the formaldehyde is washed out from the gas mixture advantageously countercurrently.

Formaldehyde prepared by the process of the invention is a disinfectant, tanning agent, reducing agent and a valuable starting material for the production of synthetic resins, adhesives and plastics. Volume 7 of Ullmann, page 670, may be referred to for utility details.

The following Examples, in which the parts are by weight, illustrate the invention.

EXAMPLE 1

A unit is used which has a methanol vaporizer and a vertical tubular reactor. The reactor hood is on top of the reactor and the vaporous starting mixture is fed in at the top. The catalyst bed is located beneath the top of the reactor and below this there is a cooling zone. The reactor is connected to an absorption column.

A catalyst of silver crystals (0.187 part) of the following composition is introduced into the reactor:

| Layer | Proportion of catalyst (% by weight) | Particle size (mm) |
|---|---|---|
| 1 | 12.9 | 0.4 to 0.75 |
| 2 | 1.2 | 0.2 to 0.4 |
| 3 | 5.3 | 0.75 to 1 |
| 4 | 14.1 | 1 to 1.75 |
| 5 | 66.5 | 1 to 2.5 |

Layer 2 is strewn as an annular layer at the periphery of the catalyst bed onto layer 3. The diameter of the catalyst bed is 170 cm and the breadth of the annular layer is 1.5 cm. A mixture of 5.15 parts of methanol in the form of crude methanol with 1.5% of impurities, 1.29 parts of water and 11.03 parts of air is supplied to, and vaporized in, the vaporizer per hour. The vaporous starting mixture is passed through the catalyst and reacted at 700° C and 1.4 atmospheres. The reaction mixture is then cooled to 150° C and dissolved in water. THe offgas consists to the extent of 0.05% by weight of formaldehyde, 6.3% by weight of steam, 1.2% by weight of hydrogen, 0.3% by weight of carbon monoxide, 7.2% by weight of carbon dioxide and 84.9% by weight of nitrogen.

4.25 parts per hour of formaldehyde (calculated 100%)—a yield of 88% of theory—is obtained in the form of a 40.2% by weight formaldehyde solution. The life of the catalyst is 110 days. The formaldehyde solution has a content of 3.25% by weight of methanol and 0.015% by weight of formic acid based on formaldehyde (calculated 100%).

EXAMPLE 2

The unit used is the same as in Example 1.
The reactor is charged with a catalyst of silver crystals (0.187 part) having the following composition:

| Layer | Proportion of catalyst (% by weight) | Particle size mm |
|---|---|---|
| 1 | 14.5 | 0.2 to 0.75 |
| 2 | 5.3 | 0.75 to 1.0 |
| 3 | 80.2 | 1.0 to 2.5 |

The reaction is carried out as in Example 1.
The composition of the offgas corresponds to that in Example 1. 4.24 parts per hour of formaldehyde (calculated 100%)—a yield of 87.8% of theory—is obtained in the form of a 40.8% by weight aqueous solution of formaldehyde. The life of the catalyst is 113 days. The formaldehyde solution contains 3.2% by weight of methanol and 0.016% by weight of formic acid, based on formaldehyde (calculated 100%).

EXAMPLE 3

The unit used is the same as in Example 1.
The reactor is charged with a catalyst of silver crystals (0.187 parts) of the following composition:

| Layer | Proportion of catalyst % by weight | Particle size mm |
|---|---|---|
| 1 | 5.1 | 0.6 to 0.75 |
| 2 | 8.3 | 0.4 to 0.6 |
| 3 | 1.5 | 0.2 to 0.4 |
| 4 | 5.5 | 0.75 to 1 |
| 5 | 11.1 | 1 to 1.5 |
| 6 | 34.0 | 1.5 to 2 |

| Layer | Proportion of catalyst % by weight | Particle size mm |
|---|---|---|
| 7 | 34.5 | 2 to 2.5 |

Layer 3 is strewn onto layer 4 as an annular layer at the periphery. The reaction is carried out as in Example 1.

The composition of the offgas corresponds to that in Example 1. 4.25 parts per hour of formaldehyde (calculated 100%)—a yield of 88% of theory—is obtained in the form of a 40.0% by weight aqueous formaldehyde solution. The life of the catalyst is 105 days. The formaldehyde solution has a content of 3.1% by weight of methanol and 0.015% by weight of formic acid based on formaldehyde (calculated 100%).

We claim:

1. In a process for the production of formaldehyde by oxidative dehydrogenation of methanol vapor with oxygen gas in the presence of a silver catalyst at elevated temperature, the improvement which comprises carrying out the reaction by passing the reacting methanol and oxygen gases downwardly through a layered catalyst bed having a total catalyst thickness of from 15 to 35 mm. the catalyst bed being maintained in three superimposed portions, each of which consist of one or more layers of catalyst particles differing in size from layer to layer, with the proviso that the lower portion contains from 72.5 to 89% by weight of the catalyst as particles of a particle size of from 1 to 2.5 mm. the central portion contains 2.5 to 7.5% by weight of the catalyst as particles of a particle size of from 0.75 to 1 mm. and the remaining upper portion contains from 8.5 to 20% by weight of the catalyst as particles of a particle size of from 0.2 to 0.75 mm.

2. A process as claimed in claim 1 wherein the reaction is carried out with a catalyst having a total layer thickness of from 20 to 30 mm.

3. A process as claimed in claim 1 wherein the reaction is carried out with a catalyst having from four to seven layers.

4. A process as claimed in claim 1 wherein the reaction is carried out with a catalyst in which the upper portion has two layers of which the lower layer has a proportion of 0.5 to 2% by weight of all the catalyst particles having a particle size of from 0.2 to 0.4 mm and of which the upper layer has a proportion of from 8 to 18% by weight of all the catalyst particles having a particle size of from 0.4 to 0.75 mm; in which the central portion has two layers of which the upper layer contains 1.5 to 4.5% by weight of all the catalyst particles having a particle size of from 0.75 to 0.9 mm and the lower layer has 1 to 3% by weight of all the catalyst particles having a particle size of from 0.9 to 1 mm; and in which the bottom portion has two layers of which the upper layer contains 7.5 to 22.5% by weight of all the catalyst particles having a particle size of from 1 to 1.75 mm and the lower layer contains 50 to 81.5% by weight of all the catalyst particles having a particle size of from 1 to 2.5 mm.

5. A process as claimed in claim 1 wherein the reaction is carried out with a catalyst in which three layers are present in each of the three portions, the proportion of the weight of the total catalyst (and particle size of the particles) being as follows: for the top portion 0.5 to 2% by weight (0.2 to 0.4 mm) in the lower layer, 5 to 10% by weight (0.4 to 0.6 mm) in the central layer, and 3 to 8% by weight (0.6 to 0.75 mm) in the upper layer; for the central portion, upper layer 0.5 to 1.5% by weight (0.75 to 0.8 mm); central layer 1 to 3% by weight (0.8 to 0.9 mm); lower layer 1 to 3% by weight (0.9 to 1 mm); and for the lower portion, upper layer 5 to 16.5% by weight (1 to 1.5 mm); central layer 28 to 42% by weight (1.5 to 2.0 mm); and lower layer 28 to 42% by weight (2.0 to 2.5 mm).

6. A process as claimed in claim 1 wherein the reaction is carried out with a catalyst in which one individual layer is superposed only at the periphery of the catalyst zone in the form of an annular layer having a level upper and lower side on a uniform layer and the breadth of the annular layer (i.e. the difference between the radius of the outer circle and the radius of the inner circle of the annular layer) is from one-hundredth to one-tenth of the radius of the catalyst layer.

7. A process as claimed in claim 1 wherein the reaction is carried out with a catalyst in which layer (2) is an annular layer and is positioned beneath layer (1) and therefore on layer (3) and in which the layers of the catalyst have the following compositions:

Layer (1): (the uppermost layer)
  8 to 18% by weight of the catalyst with particles of a particle size of from 0.4 to 0.75 mm;

Layer (2):
  0.5 to 2% by weight of the catalyst with particles of a particle size of from 0.2 to 0.4 mm;

Layer (3):
  2.5 to 7.5% by weight of the catalyst with particles of a particle size of from 0.75 to 1.0 mm;

Layer (4):
  7.5 to 22.5% by weight of the catalyst with particles of a particle size of from 1.0 to 1.75 mm; and Layer (5): (the lowermost layer)
  50 to 81.5% by weight of the catalyst with particles of a particle size of from 1.0 to 2.5 mm.

8. A process as claimed in claim 1 wherein from 1.4 to 2.4 metric tons of methanol per square meter of catalyst cross-section is passed through the catalyst per hour.

9. A process as claimed in claim 1 wherein the reaction is carried out at a temperature of from about 550° to 750° C and at a pressure of from 0.5 to 2 atmospheres.

10. A process as claimed in claim 1 wherein the reaction is carried out with an initial mixture consisting essentially of methanol vapor and oxygen passed downwardly through the layered catalyst so that said upper portion faces and first receives the initial mixture.

* * * * *